United States Patent [19]

Borden et al.

[11] Patent Number: 4,894,529

[45] Date of Patent: Jan. 16, 1990

[54] REAL-TIME PARTICLE COUNTER FOR LIQUIDS WITH NEBULIZER AND DRYER

[75] Inventors: Peter G. Borden, Palo Alto; Jon Munson, Sunnyvale, both of Calif.

[73] Assignee: High Yield Technology, Inc., Mountain View, Calif.

[21] Appl. No.: 267,205

[22] Filed: Nov. 3, 1988

[51] Int. Cl.⁴ .............................................. G01V 9/04
[52] U.S. Cl. .................................. 250/222.2; 356/338
[58] Field of Search ............ 250/573, 574, 575, 222.2; 356/335, 336, 337, 338, 339, 340, 341, 342, 343

[56] References Cited

U.S. PATENT DOCUMENTS 4,110,043 8/1978 Eisert ................................ 250/222.2
4,360,270 11/1982 Jeck ..................................... 356/338

OTHER PUBLICATIONS

Hinds, William C., "Production of Test Aerosols", Chapter 20, pp. 379–382, Aerosol Technology, Properties, Behavior, and Measurement of Airborne Particles.

*Primary Examiner*—David C. Nelms
*Attorney, Agent, or Firm*—Skjerven, Morrill, MacPherson, Franklin & Friel

[57] ABSTRACT

A real-time particle counter apparatus for monitoring contaminant particles in liquids includes a nebulizer, a drying chamber and a counter. The nebulizer provides an aerosol of droplets containing particles to the drying chamber, and the droplets are evaporated leaving solid particles to be counted and sized by the counter. Liquid is recirculated in a closed loop by pumping means that moves the liquid between the liquid source and the nebulizer. A constant air flow containing particles is provided to the counter and the apparatus is self-regulating so that no operator is required to maintain the level of liquid in the nebulizer.

11 Claims, 1 Drawing Sheet

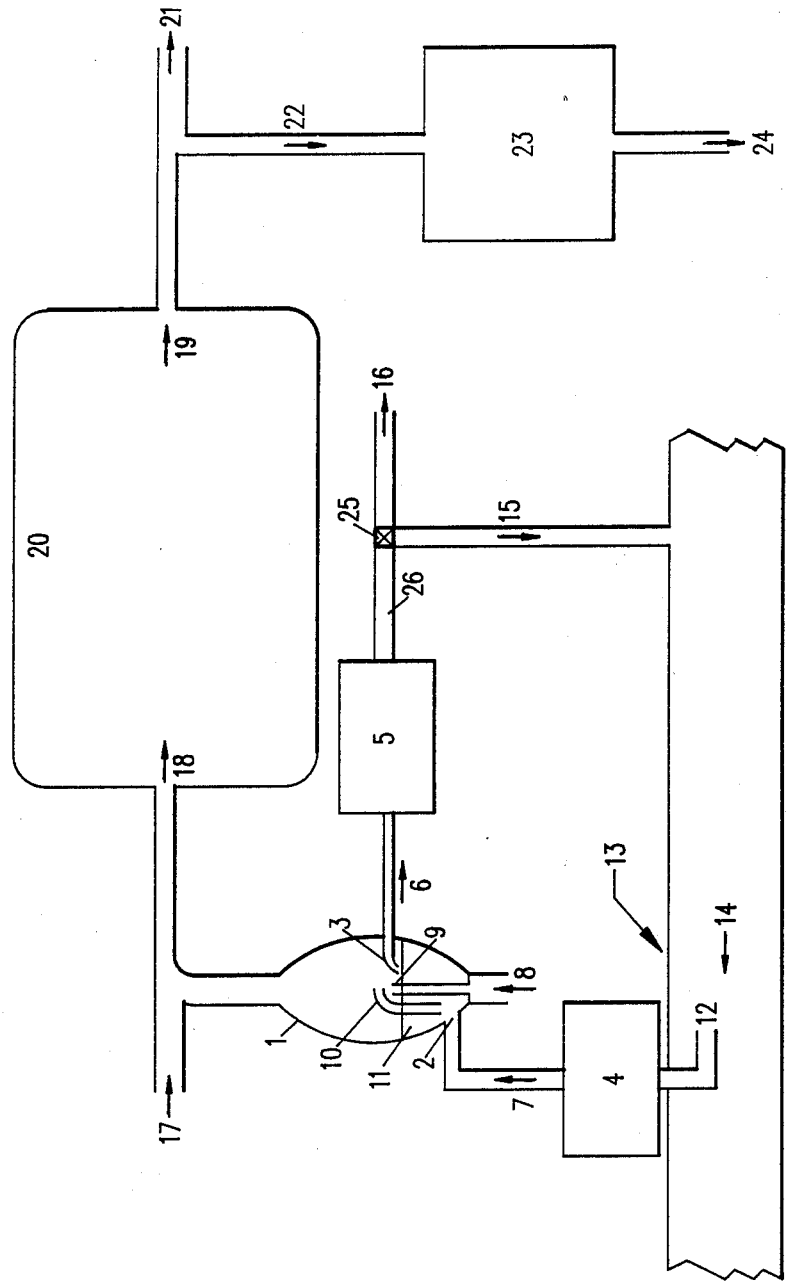

REAL-TIME PARTICLE COUNTER FOR LIQUIDS WITH NEBULIZER AND DRYER

CROSS-REFERENCE TO COPENDING APPLICATION

A particle detector for flowing liquids with the ability to distinguish bubbles is disclosed in allowed copending U.S. patent application Ser. No. 07,/012,976, filed Feb. 10, 1987, now U.S. Pat. No. 4,783,599, on behalf of Peter G. Borden, and assigned to the same assignee.

Field of the Invention

This invention relates to a particle counter for sensing particle contamination in liquids.

BACKGROUND OF THE INVENTION

Description of the Prior Art

During the manufacture of semiconductor devices, such as VLSI devices, semiconductor wafers that are being processed are exposed to liquids in a liquid bath or spray, for example. Typical liquids include deionized (DI) water, hydrogen peroxide, hydrochloric acid, hydrofluoric acid and sulphuric acid. Contamination of a liquid occurs when spurious particles enter the processing environment and become mixed in the liquid being used. These contaminants can contact and be deposited on the wafers, which would result in defective wafers thereby significantly lowering production yield.

In prior art systems, light scattering is used to detect particles by means of a very bright light beam that is directed through the liquid being sampled. If particles are present in the liquid, the light is scattered to a photodetecting means. Similar types of methods have been used to count airborne particles, such as described in the textbook by William C. Hinds, entitled "Aerosol Technology", published by John Wiley & Sons, Inc., New York, 1987.

It is known that sensitivity in liquids is much less than air, because the amount of light scattered scales as the ratio of the index of refraction of the particle to the index of refraction of the liquid medium. Although it is possible to detect particles in the 0.1 to 0.2 micron diameter size range in air, the typical detection limit in liquids is in the 0.3 to 0.5 micron size range. Therefore, it has been difficult to detect small contaminant particles that appear in liquids used for processing wafers.

An additional problem that exists in prior art particle detection systems for liquids is the presence of bubbles in the liquid. A bubble appears as a particle to the detector and thus it is generally difficult to distinguish bubbles from particle contaminants by simple light scattering technology. The conventional method to eliminate bubbles is to pressurize the liquid. This approach requires testing of the liquid sample, rather than monitoring the liquid used in the process continuously. Also, a pressurization apparatus is complex, expensive and may be dangerous to use. An improved system for distinguishing bubbles from particles in a liquid is disclosed in the aforementioned patent application.

In some particle detectors used for monitoring liquids, a nebulizer is used to aspirate the liquid and form an aerosol of small droplets. Solid particles are obtained that can be detected. In known systems that employ nebulizers, the user needs to add liquid manually to the nebulizer, by means of an eye dropper, for example. This method does not afford the monitoring of the liquid on a real-time continuous basis.

SUMMARY OF THE INVENTION

An object of this invention is to provide a particle counter useful for continuously monitoring liquids in which contaminant particles appear.

Another object of this invention is to provide a particle counter that counts very small particles in liquids without being affected by the presence of bubbles.

Another object is to provide a particle counter for detecting small contaminant particles in liquids quickly in real-time in a semiconductor wafer production line prior to the number of contaminant particles reaching high abnormal levels, thereby precluding a significant loss in production yield of semiconductor devices.

According to this invention, a particle counter for liquids incorporates, inter alia, a novel nebulizer that produces from a liquid being monitored an aerosol of small particle size, a drying chamber for evaporating the aerosol droplets to leave small particles suspended in the air of the drying chamber, and a counter for counting airborne particles drawn from the drying chamber. The air flow of contaminant particles is continuously monitored. In the event that the number of contaminant particles exceeds a predetermined level, the process is temporarily halted and the contaminated liquid is exhausted as waste and replenished with a new liquid.

BRIEF DESCRIPTION OF THE DRAWING

The sole FIGURE of the drawing is a cross-sectional elevation view, partly broken away, of the particle counter of this invention.

DETAILED DESCRIPTION OF THE INVENTION

With reference to the drawing, a liquid used in a semiconductor wafer process flows through a pipe 13, shown partially broken away. Samples of the liquid are drawn through an inlet or orifice 12 by the intake of a pump 4 and flows through a pipe 7 through an inlet port 2 into a nebulizer 1. At the same time, air is directed through an inlet 8 and is exited at an orifice 9 within the nebulizer. The orifice 9 through which the air is expelled into the nebulizer is higher than the level of liquid 11 that is pumped into the nebulizer by means of the pump 4 through the port 2. The air that is directed into the nebulizer creates a vertical jet that aspirates liquid through an orifice 10. The aspirating action creates an aerosol within the nebulizer.

The aerosol of small droplets is drawn from the nebulizer with a drying air flow that enters tube 17 and passes through an inlet 18 of a drying chamber 20, which may be a large plastic bottle, for example. The very small droplets quickly evaporate leaving small particles suspended in the air in the drying chamber. The small particles are drawn through an exit aperture 19 and flow through a pipe 22 to an airborne particle counter 23. The counter 23 includes a pump (not shown) that draws the air exiting from the drying chamber through the pipe 22. The air through pipe 22 carries the airborne particles, which are counted and sized in the airborne counter. The counter is a standard instrument commercially available for such purposes. The air through the counter exhausts through a port 24.

The sum of the volumes of air provided to the nebulizer through inlet 8 and the drying air flow provided to the drying chamber through inlet 18 is greater than the volume of air expelled at the exhaust 24 by the pump of counter 23. The difference is exhausted as excess air at exhaust 21 that is coupled to the drying chamber exit port 19, so that the air leaving the drying chamber is effectively divided into the constant flow to the counter and excess air portion.

The aerosol that is drawn from the nebulizer with the drying air flow 17 consists of water droplets having particles contained therein. Because the droplets are small in volume, the probability is very high that the droplets will each contain at most one particle. The airborne counter 23 counts and sizes these particles and provides an effective monitor to determine whether the liquid being used in the process has been unduly contaminated.

During operation of the particle counter system, if the liquid 11 in the nebulizer rises above the level of outlet port 3, liquid is drawn from the outlet port by means of a pump 5 via tube 6. The speed of pump 5 is greater than the speed of pump 4 so as to enable drawing off liquid that is higher than orifice 9 and the outlet port 3. The outlet port 3 is at lower level than the orifice 9 so that liquid does not flow down the air tube 8. A continuing flow of water is maintained through a loop including an outlet pipe 26 that is coupled to the pump 5, a return pipe 15 that is connected between the outlet pipe 26 and the main pipe 13 in which the water flows as indicated by arrow 14, the pump 4 and nebulizer 1. The liquid level in the nebulizer is thus self-regulating and does not require manual replenishment or control by the user.

In some cases, it is not desired to recirculate the liquid from the nebulizer 1 back into the main fluid flow 14. In this case, a two-way valve 25 and waste line 16 is provided, so that liquid from the nebulizer can be expelled from the system.

It should be understood that the scope of the invention is not limited to the specific configuration disclosed with reference to the drawing. In an alternate embodiment, for example, the sample orifice 12 may be disposed in a liquid bath or vat instead of in a pipe through which the liquid flows. Various types of counters may be used for counting and sizing the particles.

By means of the novel arrangement disclosed herein, a continuous flow through a nebulizer is realized to allow continuous sampling of a liquid flow and real-time counting and sizing of particles in a liquid. The novel design of the nebulizer used in the system affords self-regulation of the level of the liquid, and thereby does not require any additional operator control. Also, the evaporation of the droplets in the drying chamber virtually eliminates bubbles that may appear in liquids, but are no longer present with the remaining solid particles, so that the counter senses actual contaminants and not spurious bubbles.

What is claimed is:

1. A particle detector apparatus for detecting contaminant particles in a liquid comprising:

a source of a liquid to be monitored;

a nebulizer for aspirating said liquid to form an aerosol of droplets containing particles;

means for directing said liquid from said source to said nebulizer;

a drying chamber coupled to said nebulizer for evaporating said aerosol droplets to separate said particles in said chamber; and a particle counter coupled to said drying chamber for counting and sizing said particles.

2. A particle detector apparatus as in claim 1, including means for applying a drying air flow to said drying chamber.

3. A particle detector apparatus as in claim 1, wherein said source of liquid comprises a main pipe, including a liquid sample inlet having an opening within said main pipe.

4. A particle detector apparatus as in claim 1, wherein said means for directing said liquid to said nebulizer comprises a first pump coupled to said sample inlet, and an inlet port disposed within said nebulizer.

5. A particle detector apparatus as in claim 1, including means for introducing air to said nebulizer comprising an inlet orifice disposed in a substantially vertical orientation; and an outlet port having an opening in said nebulizer above the level of liquid in said nebulizer and below the level of said inlet orifice.

6. A particle detector apparatus as in claim 1, including a second pump coupled to said outlet port, and a return pipe coupled between said second pump and said main pipe for forming a continuous loop for the flow of liquid to said nebulizer.

7. A particle detector apparatus as in claim 6, including a pipe section coupled to the output of said second pump for exhausting waste liquid from said apparatus, and a valve for selectively controlling the flow of liquid to said return pipe for recycling the liquid in said loop or the flow of liquid to a waste exhaust means.

8. A particle detector apparatus as in claim 1, wherein said nebulizer comprises an aspirator having a first open end in said liquid and a second open end in said nebulizer above the level of said liquid.

9. A particle detector apparatus as in claim 1, wherein said counter comprises a third pump for drawing air from said drying chamber for application to said counter and for exhausting air.

10. A particle detector apparatus as in claim 9, wherein said air flowing from said drying chamber to said counter has a substantially constant level of flow.

11. A particle detector apparatus as in claim 10, including means for exhausting excess air from said drying chamber, the sum of the volumes of said excess air and exhaust air from said counter being substantially the same in volume as the sum of the air provided to said nebulizer and the air provided to said drying chamber.

* * * * *